United States Patent [19]
Engelhardt et al.

[11] Patent Number: 6,107,432
[45] Date of Patent: Aug. 22, 2000

[54] WATER-SWELLABLE, HYDROPHILIC POLYMER COMPOSITIONS

[75] Inventors: Fritz Engelhardt, Chesapeake, Va.; Rüdiger Funk, Niedernhausen, Germany; Norbert Herfert, Altenstadt, Germany; Matthias Weismantel, Jossgrund-Oberndorf, Germany

[73] Assignee: BASF AG, Germany

[21] Appl. No.: 09/084,941

[22] Filed: May 26, 1998

[30] Foreign Application Priority Data

May 28, 1997 [DE] Germany .................. 197 22 340

[51] Int. Cl.[7] .................................................. C08G 63/00
[52] U.S. Cl. ........................... 527/311; 527/313; 527/314
[58] Field of Search ................................... 527/311, 313, 527/314

[56] References Cited

U.S. PATENT DOCUMENTS

| | | |
|---|---|---|
| 4,076,663 | 2/1978 | Masuda et al. . |
| 4,454,055 | 6/1984 | Richman et al. . |
| 5,019,606 | 5/1991 | Marten et al. . |
| 5,066,745 | 11/1991 | Engelhardt et al. . |
| 5,079,354 | 1/1992 | Gross et al. . |
| 5,145,906 | 9/1992 | Chambers et al. ............... 524/732 |
| 5,219,971 | 6/1993 | Heidel et al. .................. 527/314 |
| 5,264,471 | 11/1993 | Chmelir . |
| 5,274,048 | 12/1993 | Engelhardt et al. . |
| 5,331,059 | 7/1994 | Engelhardt et al. . |
| 5,340,853 | 8/1994 | Chmelir et al. . |
| 5,594,083 | 1/1997 | Funk et al. . |
| 5,733,576 | 3/1998 | Chmelir . |

FOREIGN PATENT DOCUMENTS

| | | |
|---|---|---|
| 0339461 | 11/1989 | European Pat. Off. . |
| 0343427 | 11/1989 | European Pat. Off. . |
| 0349935 | 1/1990 | European Pat. Off. . |
| 0481370 | 4/1992 | European Pat. Off. . |
| 0543303 | 5/1993 | European Pat. Off. . |
| 0637594 | 2/1994 | European Pat. Off. . |
| 0675142 | 10/1995 | European Pat. Off. . |
| 2612846 | 10/1976 | Germany . |
| 4029591 | 3/1992 | Germany . |
| 4029592 | 3/1992 | Germany . |
| 4029593 | 3/1992 | Germany . |
| 3132976 | 4/1992 | Germany . |
| 4442605 | 6/1996 | Germany . |
| 4442606 | 6/1996 | Germany . |
| WO 94/25519 | 11/1994 | WIPO . |
| WO 94/25520 | 11/1994 | WIPO . |

OTHER PUBLICATIONS

J. Pol. Sce. vol. XXXIV, pp. 287–307 (1959).
"The Chemistry of Functional Groups, Peroxides" edited by S. Patai 1983, Chapter 13.
Makromol. Chem 1, p. 169 (1947).

*Primary Examiner*—Nathan M. Nutter
*Attorney, Agent, or Firm*—David T. Banchik

[57] ABSTRACT

The present invention relates to water-swellable, hydrophilic polymer compositions which can be prepared by free-radical (co)polymerization of one or more hydrophilic monomers in the presence of starch and/or chemically modified starch, wherein a free-radical initiator which forms three or more free radical sites per molecule is used.

9 Claims, No Drawings

WATER-SWELLABLE, HYDROPHILIC POLYMER COMPOSITIONS

The invention relates to water-swellable, hydrophilic polymer compositions of a combination of synthetic polymers and starch or chemically modified starch derivatives, processes for their preparation and their use for the preparation of hygiene articles, such as diapers, sanitary towels and incontinence articles.

Most of the absorption materials used today, which are also referred to as superabsorbents and are capable of absorbing large amounts of liquid, such as water or urine, in a short time, are primarily weakly crosslinked polyacrylates. These absorption materials are therefore not based on renewable raw materials and are biodegradable only to an insufficient extent, if at all.

In the light of the greater environmental consciousness, efforts are being made to base superabsorbents completely or partially on renewable raw materials. Suitable renewable raw materials are the polysaccharides, a very particularly suitable renewable raw material being starch. This is available in sufficiently large amounts Land, like chemically modified starch derivatives, is furthermore readily biodegradable.

Superabsorbents based on pure starch are already known. Thus, U.S. Pat. No. 5,079,354 describes an absorption material based on crosslinked carboxymethyl-starch. EP-A 637594 discloses a water-absorbent resin comprising a crosslinked polysaccharide, it being possible for the latter to be a carboxyalkylcellulose or a carboxyalkyl-starch which is crosslinked by reaction with an amino acid. DE-A 44 42 605 claims swellable starch esters which are obtainable by partial esterification of starch or modified starch with a carboxylic anhydride or a mixture of carboxylic anhydrides and crosslinking. DE-A 44 42 606 describes the preparation of superabsorbent material by reaction of starch or modified starch with one or more carboxylic anhydrides, preferably maleic anhydride. However, all superabsorbent materials based on pure starch and known to date have substantially lower absorption capacity for aqueous liquids, in particular under pressure, in comparison with the commercial polyacrylate-based superabsorbents. In the diaper structures used today, superabsorbent materials based on pure starch can therefore replace polyacrylate superabsorbents only if relatively large and in the end unacceptable losses in performance of the diapers are accepted.

In an effort to retain the absorption capacity of the pure polyacrylate superabsorbents but to increase the proportion of components composed of renewable raw materials, numerous absorption materials have been produced from polyacrylate and polysaccharides.

DE-C 26 12 846 describes graft polymers of acrylic acid on polysaccharides, such as, for example, cornstarch. However, only small amounts of polysaccharides (up to not more than 25%) can be used since otherwise the absorption properties deteriorate dramatically.

In the same way, by incorporating polysaccharides into polymerization gel of polyacrylates, as described in DE-A 40 29 591, DE-A 40 29 592 and DE-A 40 29 593, only up to at most 25% of the polyacrylates can be replaced without resulting in substantial deterioration in the absorption capacity and other properties of the resulting superabsorbents, even if various auxiliaries, such as fibers and, for example, aluminum crosslinking agents, are also added. DE-C 31 32 976 describes the mixing of polyacrylic acid with polysaccharides, preferably uncrosslinked carboxymethylcellulose, in powder form and in solution. However, no bonds at all are obtained between polyacrylic acid and polysaccharide component by the processes described herein, so that the polysaccharide component can be readily extracted again from the absorption material, thus contributes nothing more to the absorption capacity and, on the contrary, makes it more difficult to absorb liquid, owing to the increase in the viscosity of the solution surrounding the superabsorbent particles.

WO94/25519 and WO94/25520 describe polymer compositions comprising water-soluble and/or water-swellable polymers based on polysaccharides and water-swellable synthetic polymers, these polymers being crosslinked by at least one compound which is at least bifunctional. However, these polymer compositions also require the addition of matrix materials, ionic or covalent crosslinking agents and antiblocking agents for preventing separation, gel blocking and caking in humid air. By means of these additives, the absorption capacity is reduced in an undesired manner.

It is the object of the present invention to provide, in a simple manner, a water-swellable, hydrophilic polymer composition based on a synthetic polymer and starch or a chemically modified starch derivative, which composition does not have the disadvantages described above and possesses the following properties:

a) It should have as high a starch content as possible so that it is in principle at least partly biodegradable.

b) It should have as high an absorption capacity as possible for water and aqueous liquids, i.e. the starch component or starch derivative component should make an active contribution to the absorption capacity.

c) It should have as low a content as possible of extractables, i.e. the starch polymer chain or starch derivative polymer chain should be bonded to the polymer chains of the synthetic polymer to form a network.

It has now surprisingly been found that this object can be achieved by polymerization of hydrophilic monomers in the presence of starch or starch derivatives with the use of free-radical initiators which can form three or more free radical sites per molecule. The use of such free-radical initiators for the preparation of superabsorbents has already been described in EP-A 675142. However, this document provides no teaching with regard to improving the performance of products having a high content of starch or starch derivatives.

The object according to the invention is thus achieved by a water-swellable, hydrophilic polymer composition which can be prepared by free-radical (co)polymerization of one or more hydrophilic monomers in the presence of starch and/or chemically modified starch, wherein a free-radical initiator which forms three or more free radical sites per molecule is used.

The weight ratio of synthetic polymer component, i.e. polymer component obtained from hydrophilic monomers, to starch component or starch derivative component is in particular from 90:10 to 10:90, preferably from 70:30 to 20:80, and particularly preferably from 60:40 to 30:70.

Suitable hydrophilic monomers are, for example, polymerizable acids, such as acrylic acid, methacrylic acid, caproic acid, vinylsulfonic acid, vinylphosphonic acid, maleic acid, including its anhydride, fumaric acid, itaconic acid, 2-acrylamido-2-methylpropanesulfonic acid and their amides, hydroxyalkyl esters and esters and amides containing amino groups or ammonium groups, and furthermore, water-soluble N-vinylamides or diallyldimethylammonium chloride.

Preferred hydrophilic monomers are compounds of the general formula I

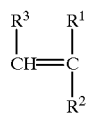

(I)

in which
R$^1$ is hydrogen, methyl or ethyl,
R$^2$ is the group—COOR$^4$, the sulfonyl group, the phosphonyl group, the phosphonyl group esterified with (C$_1$–C$_4$)-alkanol or a group of the formula

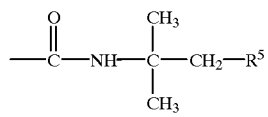

R$^3$ is hydrogen, methyl, ethyl or the carboxyl group,
R$^4$ is hydrogen, amino or hydroxy-(C$_1$–C$_4$)-alkyl and
R$^5$ is the sulfonyl group, the phosphonyl group or the carboxyl group.

Particularly preferred hydrophilic monomers are acrylic acid and methacrylic acid.

Suitable starches are in principle all starches which can be generated from natural resources. Examples are natural or pregelatinized cornstarch, natural or pregelatinized waxy cornstarch, natural or pregelatinized potato starch, natural or pregelatinized wheat starch, natural or pregelatinized amylo cornstarch or natural or pregelatinized tapioca starch. Pregelatinized cornstarch and pregelatinized potato starch are particularly preferred.

Suitable chemically modified starches are, for example, starches degraded by acid catalysis, enzymatically or thermally, oxidized starches, starch ethers, such as, for example, allyl starch or hydroxyalkyl starches, such as 2-hydroxyethyl starches, 2-hydroxypropyl starches or 2-hydroxy-3-trimethylammoniopropyl starches, or carboxyalkyl starches, such as carboxymethyl starches, starch esters, such as, for example, monocarboxylic esters of starch, such as starch formates, starch acetates, starch acrylates, starch methacrylates or starch benzoates, starch esters of di- and polycarboxylic acids, such as starch succinates or starch maleates, starch carbamic acid esters (starch urethanes), starch dithiocarbonic acid esters (starch xanthogenates), or starch esters of inorganic acids, such as starch sulfates, starch nitrates or starch phosphates, starch ester ethers, such as, for example, 2-hydroxyalkyl-starch acetates, or full acetals of starch, as formed, for example, in the reaction of starch with aliphatic or cyclic vinyl ethers. Carboxymethyl-starches, starch succinates or starch maleates are particularly preferred.

In principle, all compounds which form three or more free radical sites per molecule with or without the action of additional activators, such as light, radiation, heat, ultrasonics, redox compositions, etc., can be used as free-radical initiators. This means that these free-radical initiators contain three, four or more groups which are capable of forming free radicals. The free radical sites may be formed simultaneously but as a rule are formed at different times, i.e. in succession. For example, compounds which contain at least three hydroperoxide units, peroxide units or azo units are suitable.

For example, polyhydroperoxides which can be obtained by anodic oxidation of polycarboxylic acids, in particular of polyacrylic acid and polymethacrylic acid, in the presence of oxygen are suitable (J. Pol. Sci. Vol. XXXIV, pages 287 to 307 (1959)).

Peroxide units may be present, for example, as percarbonate, perketal or perester units. Examples of such compounds are in particular dioxetane compounds and tert-butyl peresters, such as, for example, methacrylate/tert-butyl peracrylate copolymers (J. Pol. Sci. Vol. XXXIV, page 301 (1959)).

Besides, "The Chemistry of Functional Groups, Peroxides", edited by S. Patai 1983, John Wiley & Sons Ltd., Chapter 13, by Ray Ceresa, describes suitable compounds having a plurality of peroxide or hydroperoxide units and syntheses. The content of this publication is hereby expressly incorporated in the present disclosure.

It is preferable if free-radical initiators containing hydroperoxide or peroxide units are used in combination with reducing agents. Suitable reducing agents are, for example, Fe$^{2+}$, ascorbic acid, sulfinic acid, sulfites and formamidine-sulfinic acids and salts thereof.

Suitable compounds which contain three or more azo units are, for example, reaction products of a) Azodicarboxylic acids with compounds which contain more than two oxirane functions. Depending on the oxirane compound used, trimeric to oligomeric compounds and polymers can be obtained in this manner. A preferred azodicarboxylic acid is in particular 4,4'-azobis(4-cyanovaleric acid), which forms suitable free-radical initiators, for example, with polyglyceryl polyglycidyl ethers.

b) azo compounds having hydroxyl and amino functions with compounds which contain more than two oxirane groups. Suitable azo compounds are, for example, 2,2'-azobis(N,N-dimethyleneisobutyramidine) or the corresponding dihydrochloride, 2,2'-azobis(2-amidinopropane) dihydrochloride, 2,2'-azobis(2-methyl-N-(1,1-bis(hydrox)(methyl)-2-hydroxyethyl)propionamide), 2,2'-azobis(2-methyl-N-(1,1-bis(hydroxy-methyl)ethyl)propionamide) or 2,2'-azobis(2-methyl-N-(2-hydroxy-ethyl)propionamide), which form suitable free-radical initiators, for example, with to polyglycidyl ethers mentioned above under a).

c) Azobisnitriles with tri- or polyalcohols. In particular, reaction products of 2,2'-azobisisobutyronitrile with glycerol, trimethylolpropane, threitol, erythritol, pentaerrythritol, arabitol, adonitol, xylitol, sorbitol, mannitol or dulcitol are preferred.

The stated free-radical initiators may be used alone or in any desired mixtures with one another for the preparation of the water-swellable, hydrophilic polymer composition according to the invention.

They are preferably used in amounts of from 0.001 to 20% by weight, based on the total monomers. From 0.05 to 3.0% by weight are particularly preferred.

In a particular embodiment of the present invention, free-radical initiators whose functions forming free radicals have different reactivities or are activated by different mechanisms are used. Such initiators thus contain, for example, both azo and peroxide or hydroperoxide functions which are activated in succession in a predetermined manner and can therefore be used, for the preparation of block polymers.

It may furthermore be advantageous to use initiators whose free radical-forming functions are different distances apart in the molecule.

The molecular weight of the initiators which may be used for the preparation of polymer compositions according to the invention can of course vary within wide limits. The molecular weights are in particular in the range from 100 to 1 10,000,000.

The polymer compositions according to the invention can also be prepared using suitable crosslinking agents, i.e. compounds having at least two double bonds which can be incorporated by polymerization into the network of the synthetic polymer component.

Suitable crosslinking agents are in particular methylenebisacrylamide and methylenebismethacrylamide, esters of unsaturated mono- or polycarboxylic acid with polyols, such as diacrylate or triacrylate, e.g. butanediol or ethylene glycol diacrylate or dimethacrylate, trimethylolpropane triacrylate and vinyl methacrylate, and allyl compounds, such as allyl (meth)acrylate, triallyl cyanurate, diallyl maleate, polyallyl esters, allyl ethers of polyols, such as, for example, pentaerythrityl di- and triallyl ethers, tetraallyloxyethanes, triallylamine, tetraallylethylenediamine, allyl esters of phosphoric acid and vinylphosphonic acid derivatives, as described, for example, in EP-A 343427. The content of EP-A 343427 is also expressly incorporated in the present disclosure.

The content of crosslinking agent is preferably from 0 to 20% by weight, particularly preferably from 0 to 3% by weight, based on the total monomer content.

In addition, the polymer compositions according to the invention may be postcrosslinked in a manner known per se in the aqueous gel phase and/or surface-crosslinked as milled and sieved polymer particles. Crosslinking agents suitable for this purpose are compounds which contain at least two groups which are capable of forming covalent bonds with the carboxyl groups and/or the hydroxyl groups of the polymer composition. Suitable compounds are, for example, di- or polyglycidyl compounds, such as diglycidyl phosphonates, alkoxysilyl compounds, polyaziridines, polyamines, polyamidoamines and their reaction products with epichlorohydrin, di- or polyalcohols, divinyl sulfone or di- or polyaldehydes, such as, for example, glyoxal. Particularly suitable crosslinking agents are diglycidyl phosphonate, as described in EP-A 481370 and EP-A 543303, and polyamidoamine/epichlorhydrin adducts, as described in particular in EP-A 349935. The content of the abovementioned patent applications is also expressly incorporated in the present disclosure.

The water-swellable, hydrophilic polymer compositions according to the invention can be prepared by known polymerization methods, for example by polymerization in the aqueous phase by the inverse suspension polymerization method. However, polymerization in aqueous solution by the so-called gel polymerization method is particularly preferred. Aqueous solutions having a solids content of from 15 to 60% by weight are polymerized in the presence of a free-radical initiator capable of forming tri- or polyradicals, preferably without mechanical mixing and with the utilization of the Trommsdorff-Norrish effect (Bios Final Rep. 363.22; Makromol. Chem. 1, 169 (1947)).

The polymerization reaction can be carried out in the temperature range between 0° C. and 130° C., preferably between 10 and 100° C., both at atmospheric pressure and under superatmospheric pressure. As usual, the polymerization can also be effected in an inert gas atmosphere, preferably under nitrogen. The quality properties of the polymers can be further improved by subsequently heating the aqueous polymer gels for several hours in the temperature range from 50 to 130° C., preferably from 70 to 100° C.

The polymer compositions according to the invention which are prepared n this manner and are present in the form of aqueous gels can, after mechanical comminution by means of suitable apparatuses, be obtained in solid form by known drying methods and can be used. A particularly preferred drying method here is the drum drying method which permits gentle drying of the product in a short time.

The water-swellable, hydrophilic polymer compositions according to the invention are based partly on renewable raw materials, are partly biodegradable and have substantial advantages in comparison with known starch/polyacrylate polymer compositions of the prior art. In particular, they have a low content of extractables, stronger binding of the starch polymer chains to the polyacrylate network and a higher contribution by the starch polymer component to the swelling properties. They therefore have a high liquid binding capacity in combination with high liquid retention values and high mechanical strength of swollen gel particles as well as high permeability of swollen gel layers.

They are therefore outstandingly suitable as absorption compositions for water and aqueous liquids, such as urine or blood, in hygiene articles, such as babies' and adults' diapers, sanitary towels, tampons and the like. However, they can also be used as soil conditioners in agriculture and horticulture, as moisture binders in cable sheaths and for thickening aqueous wastes.

Description of the Test Methods Used in the Examples

FSC (Free Swell Capacity):

To determine the FSC, 0.2 g of absorbent product (SAP) (particle fraction 106–850 $\mu$m) are weighed into a tea bag measuring 60×60 mm, which is then welded. The tea bag is then introduced into an excess of 0.9% strength by weight sodium chloride solution (at least 1.25 l of sodium chloride solution/1 g of SAP). After a swelling time of 20 minutes, the tea bag is removed from the sodium chloride solution and the excess solution is allowed to drip off for 10 minutes. The amount of liquid absorbed by the SAP is then determined by weighing the tea bag.

CRC (Centrifuge Retention Capacity):

To determine the CRC, 0.2 g of SAP (particle fraction 106–850 $\mu$m) are weighed into a tea bag measuring 60×60 mm, which is then welded. The tea bag is then placed in an excess of 0.9% strength by weight sodium chloride solution (at least 1.25 l of sodium chloride solution/1 g of SAP). After a swelling time of 20 minutes, the tea bag is removed from the sodium chloride solution and centrifuged at 250 g for three minutes. The amount of liquid retained by the SAP is determined by weighing the centrifuged tea bag.

Extractables:

To determine the extractables, 1 g of SAP (particle fraction 106–850 $\mu$m) are stirred into 200 g of 0.9% strength by weight sodium chloride solution. The mixture is stirred for 1 hour and then filtered. An aliquot of filtrate is dried to constant weight in a drying oven at about 105–110° C. with gentle air throughput. The extractables can be determined by weighing the residue, taking into account the sodium chloride content of the solution.

AUL (Absorbency under Load):

The absorption under load (AUL) was determined in a known manner, as described, for example, in EP-A 339 461. Here, the AUL 20 relates to the measurement of the absorbency under a load of 20 g/cm$^2$ and the AUL 40 relates to the measurement of the absorbency under a load of 40 g/cm$^2$, the occupancy of the superabsorbent particles (particle fraction 300–600 $\mu$m) per unit area in the measuring cell being 0.032 g/cm$^2$.

Preparation of the Free-radical Initiators a) Preparaton of a polyfunctional azoinitiator: Apparatus: glass autoclave with stirrer, internal thermometer, HCl inlet valve and pressure manometer. 164.2 g (1.0 mol) of 2,2'-azobisisobutyronitrile in 400 ml of chloroform were added to 33.5 g (0.25 mol) of trimethylolpropane in 300 ml of dry chloroform. The reaction mixture was cooled to 2° C. with stirring. HCl gas was passed into the autoclave and, after the solution had been saturated with the gas, an excess HCl pressure of 4 bar was established. After 48 h at 2° C., the excess HCl pressure was let down and the reaction mixture was added to 600 ml of ice water. The organic phase was separated off, washed with saturated NaCl solution and neutralized with saturated NaHCO$_3$ solution. The organic phase was then dried over Na$_2$SO$_4$ and the solvent was distilled off at room temperature under reduced pressure from an oil pump. A waxy solid yellow product was isolated.

b) Preparation of a polyfunctional free-radical initiator:

Apparatus: Double-jacketed beaker-type electrolysis cell having a lateral ground glass joint, Teflon stopper with holes for electrodes, gas inlet tube and thermometer, Pt plate electrodes on holder; cryostat; galvanostat with current supply lines, measuring instruments, etc.

0.35 g of NaOH (0.0086 mol) was added to 150 g of an aqueous solution which contained 8.3% (12.45 g, 0.173 mole equivalent of COOH) of polyacrylic acid (M$_w$=about. 200,000) and the mixture was transferred to the electrolysis cell and thermostated at 10° C. with the aid of a cryostat. A steady O$_2$ stream was then passed into the solution via the gas inlet tube, onto its lower end a glass frit had been fused. Electrolysis was carried out with stirring at a current of 150 mA up to a charge throughput of 1800 C., the internal temperature being maintained at 10° C. and the electrolyte being continuously flushed with oxygen. The electrolysis product was used in this form directly for polymerization experiments.

Comparative example 1

2220 g of demineralized water are taken in a polyethylene vessel well insulated by foamed plastics material and having a capacity of 10 l, 752.5 g of sodium bicarbonate are suspended therein and 990 g of acrylic acid are metered in slowly so that frothing over of the reaction solution is avoided, said solution being cooled to a temperature of about 5 to 3° C. 4 g of trimeethylolpropane triacrylate and a solution of 1210 g of the starches or starch derivatives stated in Table 1 in 3020 g of cooled water are then added. Nitrogen is passed through this solution until a residual oxygen content of 2 ppm is reached. Initiators are added in succession at a temperature of 4° C. and thoroughly stirred. A thermal initiator, 2.6 g of 2,2'-azobisamidinopropane dihydrochloride, dissolved in 20 g of demineralized water, and a redox initiator system, 0.8 g of potassium persulfate, dissolved in 170 g of demineralized water, and 0.4 g of ascorbic acid, dissolved in 120 g of demineralized water, are used. The reaction solution is then allowed to stand without stirring, a solid gel forming as a result of the incipient polymerization, in the course of which the temperature increases to about 60° C. Said gel is then mechanically comminuted, dried with the aid of a drum dryer, milled and sieved to 100 to 850 μm. The products have the following physical data:

TABLE 1

| Starch derivative | FSC | CRC | Extractables |
|---|---|---|---|
| EMOX D 30 S | 29 g/g | 21 g/g | 30.1% |
| EMCOL H7 | 31 g/g | 22 g/g | 28.2% |

TABLE 1-continued

| Starch derivative | FSC | CRC | Extractables |
|---|---|---|---|
| C*PUR 01915 | 32 g/g | 21 g/g | 35.4% |
| Primojel | 33 g/g | 23 g/g | 31.8% |
| Succinate starch (DS = 0.05) | 32 g/g | 23 g/g | 29.5% |
| Solviton N | 27 g/g | 18 g/g | 25.4% |

EMOX D 30 S oxidized starch from Emsland-Stärke
EMCOL H7: hydroxypropyl starch from Emsland-Stärke
C*PUR 01915: enzymatically degraded starch
Primojel: carboxymethyl-starch from AVEBE
Solviton N: 2-hydroxy-3-trimethylammoniopropyl starch from AVEBE The products obtained were modified in a further step by surface crosslinking. For this purpose, 50 g of each product were mixed in a cake mixer with a solution of 0.05 g of diglycidyl methylphosphonate, 0.05 g of nonaethylene glycol diglycidyl ether and 1.9 g of water. The products were then heated at 120° C. in a drying oven for 60 minutes. The following physical data were obtained:

TABLE 2

| Starch derivatives | CRC | AUL 20 | AUL 40 |
|---|---|---|---|
| EMOX D 30 S | 18 g/g | 16 g/g | 10 g/g |
| EMCOL H7 | 17 g/g | 16 g/g | 11 g/g |
| C*PUR 01915 | 17 g/g | 14 g/g | 8 g/g |
| Primojel | 18 g/g | 17 g/g | 11 g/g |
| Succinate starch (DS = 0.05) | 18 g/g | 17 g/g | 10 g/g |
| Solviton N | 14 g/g | 12 g/g | 9 g/g |

EXAMPLE 1

The procedure is as stated in the comparative example, except that 2.9 g of the polyfunctional free-radical initiator obtained as described above under a) are used instead of 2,2'-azobisamidinopropane dihydrochloride as the thermal initiator, 60 g of the electrolysis product obtained as described above under b) are used instead of potassium persulfatelascorbic acid as the redox initiator system, and 0.4 g of ascorbic acid, dissolved in 120 g of demineralized water, are employed. Table 3 shows the physical data obtained for the product before surface crosslinking:

TABLE 3

| Starch derivative | FSC | CRC | Extractables |
|---|---|---|---|
| EMOX D 30 S | 30 g/g | 21 g/g | 20.1% |
| EMCOL H7 | 31 g/g | 23 g/g | 19.3% |
| C*PUR 01915 | 32 g/g | 22 g/g | 22.7% |
| Primojel | 34 g/g | 24 g/g | 21.5% |
| Succinate starch (DS = 0.05) | 31 g/g | 23 g/g | 19.0% |
| Solviton N | 25 g/g | 19 g/g | 16.4% |

As a comparison of Tables 1 and 3 shows, products having a lower content of extractables are obtained when the polyfunctional free-radical initiator is used.

The products obtained were modified analogously to the comparative example by surface crosslinking. The following physical data were obtained:

TABLE 4

| Starch derivative | CRC | AUL 20 | AUL 40 |
|---|---|---|---|
| EMOX D 30 S | 18 g/g | 17 g/g | 12 g/g |
| EMCOL H7 | 18 g/g | 18 g/g | 12 g/g |
| C*PUR 01915 | 17 g/g | 16 g/g | 10 g/g |
| Primojel | 19 g/g | 19 g/g | 13 g/g |
| Succinate starch (DS = 0.05) | 18 g/g | 19 g/g | 13 g/g |
| Solviton N | 15 g/g | 14 g/g | 11 g/g |

As a comparison of Tables 2 and 4 shows, products having higher AUL 20 and AUL 40 values are obtained when the polyfunctional free-radical initiator is used.

COMPARATIVE EXAMPLE 2

558 g of acrylic acid, 1.28 g of tetraallyloxyethane and 292 g of the starches stated in Table 5 are taken under adiabatic conditions in a 5 l cylindrical wide-necked reaction flask. 4060 g of demineralized water cooled to 1 5° C. are taken in a second reaction flask and nitrogen is passed in. At an oxygen content of about 1.5 ppm, 10 g of a 4% strength aqueous solution of 2,2'-azobis(2-amidinopropane) dihydrochloride are added, 8 g of a 0.75% strength hydrogen peroxide solution are added after further introduction of nitrogen and at an oxygen content of about 1.3 ppm, and finally 8 g of a 0.15% strength ascorbic acid solution are added at an oxygen content of <1.0 ppm. This solution is then transferred to the mixture of acrylic acid, tetraallyloxyethane and starch in the first wide-necked reaction flask. A solid gel forms as a result of incipient polymerization, in the course of which the temperature increases to about 60° C., and said gel is then mechanically comminuted. 270 g of 27% strength sodium hydroxide solution are added to 1000 g of the comminuted gel (degree of neutralization with the acrylic acid =78 mol%) and the mixture is kneaded three times and then dried with the aid of a drum dryer, milled and sieved to 100 to 850 µm. The products have the following physical data:

TABLE 5

| Starch | FSC | CRC | Extractables |
|---|---|---|---|
| EMJEL E 30 | 48 g/g | 42 g/g | 24.9% |
| Primojel | 49 g/g | 43 g/g | 25.5% |
| EMJEL PG | 45 g/g | 39 g/g | 24.5% |
| Cerestar AJ 12014 | 45 g/g | 40 g/g | 23.6% |
| Farinex WM 85 | 41 g/g | 35 g/g | 29.7% |
| Cerestar Pt 20002 | 45 g/g | 39 g/g | 23.7% |
| Tapioca starch Full Past I | 50 g/g | 45 g/g | 28.9% |

EMJEL E 30: potato starch from Emsland-Stärke soluble in cold water
Primojel: carboxymethyl-starch from AVEBE
EMJEL PG: phosphate starch from Emsland-Stärke
Cerestar AJ 12014: cornstarch from Cerestar, soluble in cold water
Farinex WM 85: waxy cornstarch soluble in cold water
Cerestar Pt 20002: natural wheat starch from Cerestar
Tapioca starch Full Past I: tapioca starch soluble in cold water The products obtained are modified by surface crosslinking. For this purpose, 50 g of each product were mixed in a cake mixer with a solution of 0.01 g of diglycidyl n-propylphosphonate, 0.09 g of monoethylene glycol diglycidyl ether, 2.0 g of water and 2.0 g of isopropanol. The products were then heated in a drying oven for 60 minutes at 120° C. The following physical data were obtained:

TABLE 6

| Starch derivative | CRC | AUL 20 | AUL 40 |
|---|---|---|---|
| EMJEL E 30 | 32 g/g | 15 g/g | 12 g/g |
| Primojel | 32 g/g | 24 g/g | 15 g/g |
| EMJEL PG | 30 g/g | 23 g/g | 11 g/g |
| Cerestar AJ 12014 | 34 g/g | 25 g/g | 13 g/g |
| Farinex WM 85 | 25 g/g | 16 g/g | 10 g/g |
| Cerestar Pt 20002 | 35 g/g | 19 g/g | 12 g/g |
| Tapioca starch Full Past I | 32 g/g | 14 g/g | 9 g/g |

EXAMPLE 2

The procedure is as in Comparative Example 2, except that 40 g of the electrolysis product obtained as described above under b) are used instead of hydrogen peroxide/ascorbic acid as the redox initiator system and 8 g of a 0.15% strength ascorbic acid solution are employed. Table 7 shows the physical data obtained for the products before surface crosslinking:

TABLE 7

| Starch derivative | FSC | CRC | Extractables |
|---|---|---|---|
| EMJEL E 30 | 48 g/g | 43 g/g | 13.5% |
| Primojel | 49 g/g | 45 g/g | 13.4% |
| EMJEL PG | 47 g/g | 40 g/g | 14.0% |
| Cerestar AJ 12014 | 47 g/g | 43 g/g | 12.4% |
| Farinex WM 85 | 41 g/g | 34 g/g | 21.5% |
| Cerestar Pt 20002 | 46 g/g | 41 g/g | 16.8% |
| Tapioca starch Full Past I | 50 g/g | 44 g/g | 19.2% |

As a comparison of Tables 5 and 7 shows, products having a lower content of extractables are obtained when the polyfunctional free-radical initiator is used.

The products obtained were modified analogously to Comparative Example 2 by surface crosslinking. The following physical data were obtained:

TABLE 8

| Starch derivative | CRC | AUL 20 | AUL 40 |
|---|---|---|---|
| EMJEL E 30 | 31 g/g | 26 g/g | 14 g/g |
| Primojel | 32 g/g | 30 g/g | 23 g/g |
| EMJEL PG | 30 g/g | 27 g/g | 14 g/g |
| Cerestar AJ 12014 | 33 g/g | 28 g/g | 15 g/g |
| Farinex WM 85 | 25 g/g | 24 g/g | 13 g/g |
| Cerestar Pt 20002 | 31 g/g | 25 g/g | 14 g/g |
| Tapioca starch Full Past I | 30 g/g | 22 g/g | 12 g/g |

As a comparison of Tables 6 and 8 shows, products having higher AUL 20 and AUL 40 values are obtained when the polyfunctional free-radical initiator is used.

COMPARATIVE EXAMPLE 3

635 g of cyclohexane are taken in a 2 l polymerization flask and heated to 40 to 45° C. with stirring, after which 3.5 g of ethylcellulose (Type CN 200 from HERCULES, USA) are added. The mixture is heated to the reflux temperature while passing in a gentle stream of nitrogen. After refluxing for 25 minutes, a solution cooled to room temperature and comprising 245 g of water, 69 g of acrylic acid, 77.4 g of 50% strength potassium hydroxide solution, 161 g of the starches or starch derivatives stated in Table 9, mixed with a solution of 20 g of water, 0.15 g of ethylenediaminetetraacetic acid, 0.05 g of potassium persulfate and 0.1 g of 4,4'-azobis-4-cyanovaleric acid, is metered in by means of a metering pump in the course of 90 minutes. The reflux condenser is then replaced by a water separator and the water is distilled off azeotropically. After the beginning of the azeotropic distillation of the water, an emulsion comprising 15 g of cyclohexane, 0.5 g of water, 0.25 g of diglycidyl stearylphosphonate, 0.025 g of ethylene glycol diglycidyl ether and 0.4 g of sorbitan monolaurate is added. 318 g of water are distilled off, the solvent is filtered off from the polymer, drying is carried out for 2 hours at 105° C. in a drying oven and, if required, sieving to 100 to 850 μm is effected. The products have the following physical data:

TABLE 9

| Starch derivative | FSC | CRC | AUL 20 | AUL 40 | Extractables |
|---|---|---|---|---|---|
| Allyl starch (DS = 0.005) | 24 g/g | 15 g/g | 12 g/g | 8 g/g | 36% |
| Starch maleate (DS = 0.05) | 26 g/g | 16 g/g | 13 g/g | 9 g/g | 42% |
| Starch succinate (DS = 0.02) | 25 g/g | 15 g/g | 13 g/g | 9 g/g | 45% |
| Primojel | 27 g/g | 17 g/g | 14 g/g | 10 g/g | 39% |
| EMOX D 30 S | 22 g/g | 13 g/g | 11 g/g | 8 g/g | 47% |
| EMCOL H7 | 24 g/g | 14 g/g | 12 g/g | 8 g/g | 43% |
| EMJEL PG | 22 g/g | 13 g/g | 11 g/g | 8 g/g | 41% |

Primojel: carboxymethyl-starch from AVEBE
EMOX D 30 S: oxidized starch from Emsland-Stärke
EMCOL H7: hydroxypropyl-starch from Emsland-Stärke
EMJEL PG: phosphate starch from Emsland-Stärke

EXAMPLE 3

The procedure is as in Comparative Example 3, except that 0.35 g of the polyfunctional azoinitiator obtained as described above in a) is used instead of potassium persulfate and 4,4'-azobis-4-cyanovaleric acid as the initiator. Table 10 shows the physical data obtained for the products:

TABLE 10

| Starch derivative | FSC | CRC | AUL 20 | AUL 40 | Extractables |
|---|---|---|---|---|---|
| Allyl-starch (DS = 0.005) | 22 g/g | 14 g/g | 15 g/g | 12 g/g | 23% |
| Starch maleate (DS = 0.05) | 26 g/g | 16 g/g | 16 g/g | 12 g/g | 24% |
| Starch succinate (DS = 0.02) | 25 g/g | 16 g/g | 16 g/g | 13 g/g | 22% |
| Primojel | 28 g/g | 18 g/g | 18 g/g | 14 g/g | 20% |
| EMOX D 30 S | 23 g/g | 12 g/g | 13 g/g | 11 g/g | 24% |
| EMCOL H7 | 24 g/g | 14 g/g | 15 g/g | 12 g/g | 23% |
| EMJEL PG | 23 g/g | 13 g/g | 15 g/g | 12 g/g | 22% |

As a comparison of Tables 9 and 10 shows, products having a lower extractables content and higher AUL 20 and AUL 40 values are obtained when the polyfunctional free-radical initiator is used.

What is claimed is:

1. A water-swellable hydrophilic polymer composition which can be prepared by free-radical (co)polymerization of one or more hydrophilic monomers in the presence of starch and/or chemically modified starch, wherein a free-radical initiator which forms three or more free radical sites per molecule is used.

2. A water-swellable hydrophilic polymer composition as claimed in claim 1, wherein hydrophilic monomers are compounds of the general formula I

in which $R^1$ is hydrogen, methyl or ethyl, $R^2$ is the group —COOR$^4$, sulfonyl group, phosphonyl group, the phosphonyl group esterified with ($C_1$–$C_4$)-alkanol or a group of the formula

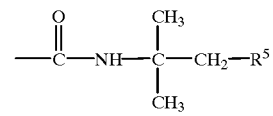

$R^3$ is hydrogen, methyl, ethyl or the carboxyl group, $R^4$ is hydrogen, amino or hydroxy-($C_1$–$C_4$)-alkyl and $R^5$ is the sulfonyl group, the phosphonyl group or the carboxyl group.

3. A water-swellable hydrophilic polymer composition as claimed in claim 1, wherein the starch used comprises natural or pregelatinized corn starch, natural or pregelatinized waxy cornstarch, natural or pregelatinized potato starch, natural or pregelatinized wheat starch, natural or pregelatinized amylo cornstarch, natural or pregelatinized tapioca starch and/or the chemically modified starch used comprises starches degraded by acid catalysis, enzymatically or thermally, oxidized starches, starch ethers, such as allyl starch, or hydroxyalkyl starches, such as 2-hydroxyethyl starches, 2-hydroxypropyl starches and 2-hydroxy-3-tri-methylammoniopropyl starches, carboxylalkyl starches, such as carboxymethyl starches, starch ethers, such as starch formates, starch acetates, starch acrylate, starch methacrylate and starch benzoates, starch esters, such as starch succinates and starch maleates, starch carbamic acid esters (starch urethanes), starch dithiocarbonic acid esters (starch xanthogenates), starch esters of inorganic acids, such as starch sulfates, starch nitrates and starch phosphates, starch ester ethers, such as 2-hydroxyalkyl-starch acetates, and full acetals of starch, such as the reaction products of starch with aliphatic or cyclic vinyl ethers.

4. A water-swellable hydrophilic polymer composition as claimed in claim 1, wherein pregelatinized cornstarch or pregelatinized potato starch is used as starch and/or carboxymethyl-starch, starch succinate or starch maleate is used as the chemically modified starch.

5. A water-swellable hydrophilic polymer composition as claimed in claim 1, wherein the free-radical initiators used are compounds which contain at least three hydroperoxide units, peroxide units or azo units.

6. A water-swellable hydrophilic polymer composition as claimed in claim 1, wherein free-radical initiator used is a reaction product of azobisisobutyronitrile with trimethylolpropane.

7. A water-swellable hydrophilic polymer composition as claimed in claim 1, wherein the free-radical initiator used is a polyhydroperoxide obtained by anodic oxidation of a polycarboxylic acid in the presence of oxygen.

8. A water-swellable hydrophilic polymer composition as claimed in claim 1, which is prepared using a crosslinking agent.

9. A process for the preparation of water-swellable hydrophilic polymer compositions as claimed in claim 1, wherein a 15 to 60% by weight aqueous solution of one or more hydrophilic monomers is polymerized in the presence of starch and/or chemically modified starch by the gel polymerization method in the presence of a free-radical initiator capable of forming tri- or polyradicals.

* * * * *